United States Patent
Jadhav

(10) Patent No.: US 9,334,234 B2
(45) Date of Patent: May 10, 2016

(54) METHOD USING TITANIUM CATALYST FOR PRODUCING CARBAMATE-FUNCTIONAL MATERIALS

(71) Applicant: BASF Coatings GmbH, Muenster (DE)

(72) Inventor: Abhijit V. Jadhav, Mangalore (IN)

(73) Assignee: BASF Coatings GmbH, Muenster (DE)

( * ) Notice: Subject to any disclaimer, the term of this patent is extended or adjusted under 35 U.S.C. 154(b) by 77 days.

(21) Appl. No.: 14/272,597

(22) Filed: May 8, 2014

(65) Prior Publication Data

US 2015/0321999 A1 Nov. 12, 2015

(51) Int. Cl.
*C08F 8/30* (2006.01)
*C07C 269/00* (2006.01)
*C08F 220/36* (2006.01)
*C09D 133/14* (2006.01)
*C07C 269/06* (2006.01)
*C08G 71/04* (2006.01)
*C09D 175/04* (2006.01)

(52) U.S. Cl.
CPC ............. *C07C 269/00* (2013.01); *C07C 269/06* (2013.01); *C08F 8/30* (2013.01); *C08F 220/36* (2013.01); *C08G 71/04* (2013.01); *C09D 133/14* (2013.01); *C09D 175/04* (2013.01)

(58) Field of Classification Search
None
See application file for complete search history.

(56) References Cited

U.S. PATENT DOCUMENTS

| 4,631,320 | A | * | 12/1986 | Parekh | C09D 201/025 427/372.2 |
| 6,306,965 | B1 | * | 10/2001 | Anderson | C08F 220/36 525/100 |
| 2003/0130471 | A1 | * | 7/2003 | Grandhee | C08G 18/3278 528/60 |

OTHER PUBLICATIONS

Shapiro, J. Org. Chem. 1997, 62, 7096-7097.*

* cited by examiner

*Primary Examiner* — Robert C Boyle
(74) *Attorney, Agent, or Firm* — Servilla Whitney LLC

(57) ABSTRACT

A carbamate-functional material is prepared by reacting a carbamate compound with a hydroxy-functional material using titanium (IV) alkoxide as catalyst.

17 Claims, No Drawings

METHOD USING TITANIUM CATALYST FOR PRODUCING CARBAMATE-FUNCTIONAL MATERIALS

FIELD OF THE INVENTION

The invention concerns methods for making materials that have carbamate functionality, particularly for use in thermosetting coatings.

BACKGROUND

This section provides information helpful in understanding the invention but that is not necessarily prior art.

Binder materials having carbamate groups have been used in thermosetting coating composition, for instance automotive clearcoat compositions. Such binder materials may be cured with relatively low viscosity aminoplast resins, which allow the coating formulations to have higher solids, to form cured coating with excellent durability, including resistance to scratching, marring, and weathering degradation. Carbamate groups may be introduced onto a binder material by reaction of a hydroxyl-functional material with an alkyl carbamate, for example methyl carbamate or butyl carbamate, through what is referred to as "transcarbamation" or "transcarbamoylation."

Tin-based catalysts have been the preferred catalysts for performing transcarbamation due to high yields. However, regulation of tin catalysts, particularly in Europe, makes it desirable to not use tin catalysts. Moreover, using tin catalysts tends to result in an unwanted increase in molecular weight of resins from catalysis of side reactions. Finally, an increase in yellowing has been noted when tin catalysts are used.

SUMMARY OF THE DISCLOSURE

A carbamate-functional material is prepared by reacting a carbamate compound with a hydroxy-functional material using a titanium (IV) alkoxide as catalyst. The hydroxy-functional material may be a monomeric compound, a resin, or a polymer and may have one or a plurality of hydroxyl groups. Carbamate groups may be represented by the structure

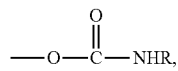

in which R is H or alkyl, preferably H or alkyl of 1 to 4 carbon atoms. Preferably R is H or methyl, and more preferably R is H. The carbamate compound has a carbamate group.

The carbamate-functional materials produced using the titanium (IV) alkoxide catalyst may be used in coating compositions, particularly for a clearcoat layer or monocoat topcoat of automotive OEM finishes and refinishes, that lead to coatings having a combination of high scratch resistance, good acid resistance, and good weathering stability that are free from tin compounds.

In various embodiments, the titanium (IV) alkoxide catalyst is one or more of titanium (IV) alkoxides in which each alkoxide group has one to eight carbon atoms. The titanium (IV) alkoxide catalyst has n alkoxide groups, where n is an integer from one to four, and has 4-n groups selected from halogen groups, acetylacetonate groups, and ethanolaminato groups.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment. The terms "comprises," "comprising," "including," and "having," are inclusive and therefore specify the presence of stated items, but do not preclude the presence of other items. As used in this specification, using the term "or" includes any and all combinations of one or more of the listed items.

DETAILED DESCRIPTION

A detailed description of exemplary, nonlimiting embodiments follows.

A carbamate-functional material is prepared by reacting a carbamate compound with a hydroxy-functional material in the presence of titanium (IV) alkoxide.

Carbamate Compound

The carbamate compound is an alkyl carbamate in which the carbamate group has a structure

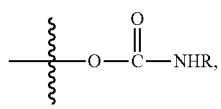

in which R is H or alkyl, preferably H or alkyl of 1 to 4 carbon atoms. Preferably R is H or methyl, and more preferably R is H. Nonlimiting examples of suitable carbamate compounds include methyl carbamate, ethyl carbamate, n-propyl carbamate, isopropyl carbamate, n-butyl carbamate, isobutyl carbamate, tert-butyl carbamate, n-hexyl carbamate, 2-ethylhexyl carbamate, cyclohexyl carbamate, phenyl carbamate, hydroxypropyl carbamate, hydroxyethyl carbamate, and combinations of these. In various embodiments, it may be preferred to use methyl carbamate.

Hydroxy-Functional Material

The hydroxy-functional material may be a monomeric compound (i.e., a compound without a backbone composed of regularly repeating units), a resin, or a polymer and may have one or a plurality of hydroxyl groups. Oligomers are polymers having relatively few monomer units; generally, "oligomer" refers to polymers with only a few monomer units, perhaps up to ten; the term "polymers" is used to encompass oligomers as well as polymers with higher numbers of monomer units. Resins may be oligomers or compounds that do not have a backbone of regularly repeating monomer units, for example higher molecular weight compounds with one or more heteroatom-containing linking groups in addition to the hydroxyl group or groups. Resins may be dendrimers, hyperbranched, or "star" resins that are prepared from a polyfunctional core compound in one or more successive generations of branching reactants having one group reactive with the functionality of the core or of the latest generation to be added to the core and one or a plurality of groups available for reaction with the next generation of branching reactant.

In various embodiments, the hydroxyl-functional material that is reacted with a carbamate compound using titanium (IV) alkoxide as catalyst may be a monomeric or oligomeric compound having at least one hydroxyl group. Such monomeric compounds include aliphatic, cycloaliphatic, and aromatic mono-alcohols and polyols that may generally have from 1 to 160 carbon atoms, preferably 1-60 carbon atoms. The monomeric and oligomeric compounds may contain only hydroxyl groups or may contain heteroatoms such as O, S, Si, N, P in other groups such as ester groups, ether groups, amino groups, or unsaturated sites. Nonlimiting examples of suitable monomeric hydroxy compounds include straight and branched mono-alcohols having 1-60 carbon atoms and optionally including heteroatoms, for example butanol, decanol, 12-hydroxystearic acid, hydroxyalkyl (meth)acrylates including hydroxypropyl (meth)acrylate and hydroxyethyl (meth)acrylate, alkylene glycol monoalkyl ethers including propylene glycol monobutyl ether and monomethyl ether, polyols such as 1,2-ethanediol, 1,3-propanediol, dimethylolpropane, 2-propyl-2-methyl-1,3-propanediol, 1,4-butanediol, 1,5-pentanediol, 1,2-hexanediol, 1,6-hexanediol, neopentyl glycol, 2-butyl-2-ethyl-1,3-propanediol, 2,2-diethyl-1,3-propanediol, 2,2,4-trimethylpentane-1,3-diol, trimethylhexane-1,6-diol, 2-methyl-1,3-propanediol, 2-ethyl-1,3-hexanediol, ethyl-propyl-1,5-pentanediol, 2-methyl-2,4-pentanediol, 2,4,7,9-tetramethyl-5-decyn-4,7-diol, 2-butene-1,4-diol, pantothenol, dimethyltartrate, 3-[(hydroxymethyl)(dimethyl)silyl]-1-propanol, 2,2'-thiodiethanol, trimethylolethane, trimethylolpropane, trimethylolbutane 1,2,6-hexanetriol, glycerol, pentaerythritol and dipentaerythritol; cycloaliphatic diols such as cyclohexane dimethanol and cyclic formals of pentaerythritol such as, for instance, 1,3-dioxane-5,5-dimethanol; aromatic polyols, for instance 1,4-xylylene glycol and 1-phenyl-1,2-ethanediol, Bisphenol A, hydroquinone, and resorcinol; and monoethers and monoesters of polyols.

In certain embodiments, the polyol may include from 12 to 72 carbon atoms, preferably from 18 to 54 carbon atoms and more preferably from 36 to 54 carbon atoms, and at least two hydroxyl groups. The polyvalent radical bearing the hydroxyl groups may be substantially free of heteroatoms. The term "heteroatoms" refers to atoms other than carbon or hydrogen; the phrase "substantially free of" heteroatoms means that the polyvalent radical will generally have no more than two atoms, preferably no more than one atom, and more preferably no atoms other than carbon or hydrogen, e.g., atoms such as N, O, and Si. The polyvalent radical may be a structure or, preferably, a mixture of two or more saturated or unsaturated structures selected from the group consisting of noncyclic structures, aromatic ring-containing structures, cycloaliphatic structures. Saturated structures are preferred, especially where durability issues are of concern. Particularly advantageous mixtures are those having from 3 to 25% by weight having an aliphatic structure, from 3 to 25% by weight having an aromatic ring-containing structure, and 50 to 94% by weight having a cycloaliphatic structures, preferably from 3 to 18% by weight having an aliphatic structure, from 5 to 23% by weight of reactive component (a) having an aromatic-containing structure, and 55 to 85% by weight of reactive component (a) having a cycloaliphatic-containing structure. Most preferred mixtures of reactive component (a) will comprise from 5 to 10% by weight of reactive component (a) having an aliphatic structure, from 10 to 20% by weight of reactive component (a) having an aromatic-containing structure, and 60 to 70% by weight of reactive component (a) having a cycloaliphatic-containing structure. Such polyol materials may be obtained by reduction of the carboxylic acid groups of dimerized, trimerized, tetramerized, or higher oligomer addition products of unsaturated fatty acids, particularly those with 12 to 18 carbon atoms. One particularly preferred polyol is a 36-carbon diol. Such materials are commercially available from Croda International Plc. under the tradename Pripol™.

The hydroxyl-functional material may be a hyperbranched polyol resin. One nonlimiting example of a suitable hyperbranched, dendritic hydroxy-functional resin is a hyperbranched, dendritic hydroxy-functional polyester prepared by successive reaction steps using reactants that are monofunctional toward a polyfunctional core but that in turn offer a plurality of functional groups that can be reacted with a different reactant to form another generation of branching. Hyperbranched, dendritic resins can be described generally as highly branched molecules. Dendrimers are highly symmetrical, whereas similar macromolecules referred to as being hyperbranched and/or dendritic may be asymmetric to a certain extent and nevertheless have highly branched, tree-like structure. Hyperbranched and dendritic resins can typically be prepared starting from an initiator or core compound having one or more reactive sites and building out from it a number of branching layers ("generations") and, if appropriate, a layer of chain-ending molecules (divergent synthesis approach). A continued replication of branching layers normally produces an increased degree of branching, and if appropriate or if desired, an increased number of end groups.

In one embodiment, a dendritic or hyperbranched polyol may be prepared by synthesis of a dendritic polymeric polyol (polyester polyol) where the polymeric polyol possesses n dendritic branches originating from a monomeric or polymeric initiator molecule having n reactive groups (A1), each branch comprising g branching generations, each generation comprising at least one polymeric or monomeric branching chain extender having three functional groups, of which at least two are reactive hydroxyl groups (A2) and one is a carboxyl group (A3) which is reactive with the reactive group (A1) and/or with the hydroxyl groups (A2), and, if desired, at least one spacer generation which comprises at least one spacer chain extender having two functional groups, of which one is a protected hydroxyl group (A2") and one is a group (A4) which is reactive with a hydroxyl group, with n and g being whole numbers and being at least 1, where (i) the two hydroxyl groups (A2) of the monomeric or polymeric chain branching extender used are acetal-protected hydroxyl groups (A2'), the protection by acetal being obtained through a reaction between the two hydroxyl groups (A2) and an acetal-forming carbonyl compound; and (ii) where a first branching generation is added to the initiator molecule through reaction between the reactive group (A1) and the carboxyl group (A3), in a molar ratio of the reactive groups (A1) to the carboxyl groups (A3) of at least 1, to give a polymeric polyol having acetal-protected hydroxyl groups (A2') and n dendritic branches which comprise one generation, the acetal-protected hydroxyl groups (A2') being deprotected, if desired, by means of acetal cleavage, to give a polymeric polyol having reactive hydroxyl groups (A2); and (iii) where further branching generations are added in g-1 repeated steps, through reaction between reactive hydroxyl groups (A2), obtained by deprotection by means of acetal cleavage, and carboxyl groups (A3), in a molar ratio of hydroxyl groups (A2) to carboxyl groups (A3) of at least 1, to give a polymeric polyol having acetal-protected hydroxyl groups (A3) and n dendritic branches which comprise two or more generations, the acetal-protected hydroxyl groups (A3) being deprotected, if desired, by means of acetal cleavage, to give a hyperbranched polyol having reactive hydroxyl groups (A2), and, if desired, (iv) step (ii) and/or each repetition of step (iii) individually is followed by (a) a partial protection, such as protection as an acetal, ketal and/or ester, for example, of available reactive hydroxyl groups (A2), giving a hyperbranched polyol having at least one reactive hydroxyl group (A2) for use in step (iii) or in a repeated step (ii), and/or (b) the addition of the optional spacer chain extender, which addition, following deprotection of the protected hydroxyl group (A2″), produces a hyperbranched polyol having reactive hydroxyl groups (A2) for use in step (iii) or in a repeated step (iii) and n dendritic branches which comprise one or more branching generations, and at least one spacer generation is at least a sub-generation. One or more but less than all of the hydroxyl groups may be esterified by reaction with a C8-C9 monocarboxylic acid, and the hydroxyl number may be at least about 180 mg KOH/g, preferably 185-240 mg KOH/g, determined in accordance with DIN 53240. The polyester polyol, furthermore, preferably possesses a number-average molecular weight of 1500-4000 g/mol, preferably 2000-3500 g/mol, determined via GPC with a polystyrene standard in THF with 0.1 mol/l acetic acid. The polyester polyol may have a low molecular weight distribution, particularly a polydispersity Mw/Mn<4 or <2 or particularly preferably the polyester polyol is monodisperse or substantially monodisperse.

In various embodiments, the hydroxy-functional material may be a hyperbranched polyol prepared by reacting a starter polyol with a plurality of hydroxyl groups with a first chain extension reactant that is a compound comprising a carboxyl group and a plurality of hydroxyl groups; then reacting the product of the first chain extension step with a second chain extension reactant that is a compound selected from the group consisting of carboxylic acid anhydrides and polyfunctional carboxylic acids or their esterifiable derivatives; then reacting the acid-functional product of the second chain extension step with a third chain extension reactant having a single epoxide group. The third chain extension reactant may have a flexible hydrocarbyl radical.

In the first chain extension step, preferred starter polyols are those having two or more reactive hydroxyl groups. The starter polyol compound can suitably be an aliphatic, a cycloaliphatic, or an aromatic diol, triol, or tetrol, or higher polyol. Suitable examples include all of the polyols mentioned above. Triols such as glycerol, trimethylolethane, trimethylolpropane, trimethylolbutane, 3,5,5-trimethyl-2,2-dihydroxymethylhexane-1-ol are examples of this type of triols. Other suitable triols are those having two types of hydroxyl groups, primary as well as secondary hydroxyl groups, as for instance glycerol and 1,2,6-hexanetriol and compounds having four or more hydroxyl groups, such as pentaerythritol, di(trimethylolpropane), and dipentaerythritol are preferred starter polyols. Also suitable as starter polyols are sugar alcohols such as sorbitol and mannitol, α-alkylglucosides such as α-methylglucoside, alkoxylate polymers having number average molecular weights of at most about 8,000 produced by reaction of an alkylene oxide or a derivative thereof and one or more hydroxyl groups from any of the alcohols mentioned above, and polyester polyols having number average molecular weights of at most about 8,000 produced by reaction of a lactone, especially epsilon-caprolactone, and one or more hydroxyl groups from any of the alcohols mentioned above. Mixtures of these can also be used as the first compound.

The first chain extension reactant has a carboxylic acid group and two or more hydroxyl groups. Nonlimiting examples of suitable first chain extension reactants include dimethylolpropionic acid, α,α-bis(hydroxymethyl)butyric acid, α,α,α-tris(hydroxymethyl)acetic acid, α,α-bis(hydroxymethyl)valeric acid, α,α-bis(hydroxyethyl)propionic acid, glyceric acid, erthronic acid, threonic acid, ribonic acid, gluconic acid, and mannonic acid. The hyperbranched polyols can be prepared by reacting the first compound and second compound under esterification conditions. The temperature of reaction is generally from 0 to 300° C., preferably 50 to 280° C., and most preferably 100 to 250° C.

Optionally, this first generation branched core may be further reacted with the first chain extension reactant one or more additional times, as desired, to cause further branching. Such additional extension of the first generation branched core, where used, forms a second, third, fourth, or higher generation branched core, as desired.

The product from the first extension reactant is reacted with a second chain extension reactant that is a compound selected from the group consisting of carboxylic acid anhydrides and polyfunctional carboxylic acids or their esterifiable derivatives to provide a carboxyl group-functional product from this step. Nonlimiting example of suitable second chain extension reactants include phthalic acid, isophthalic acid, terephthalic acid phthalic anhydride, tetrahydrophthalic anhydride, hexahydrophthalic anhydride, methylhexahydrophthalic anhydride, trimellitic anhydride, succinic anhydride, and so on.

The acid-functional product of the second chain extension step is next reacted with a third chain extension reactant having a single epoxide group to form a hyperbranched polyol macromolecule. The third chain extension reactant may have a flexible hydrocarbyl radical having a terminal or non-terminal epoxide group. Nonlimiting examples of suitable third chain extension reactants include glycidyl esters, glycidyl ethers, monoepoxide hydrocarbons, monoepoxidized acids, and monoepoxidized alcohols such as cyclohexane oxide, cis-2,3-epoxybutane, 1,2-epoxybutane, 1,2-epoxyhexane, 1,2-epoxyoctane, 1,2-epoxydecane, cis-7,8-epoxy-2-methyloctadecane, and the glycidyl esters of neoacids, particularly the glycidyl ester of neodecanoic acid. A first generation intermediate is prepared by reacting the first compound and second compound in an equivalent molar ratio of hydroxyls on the first compound to carboxyl groups on the second compound of between about 1:2 and about 2:1. Preferably the equivalent ratio will be from about 1:1.5 to about 1.5:1, and even more preferably from about 1:1.2 to about 1.2:1.

As further examples, the hydroxyl-functional materials that are reacted with a carbamate compound using titanium (IV) alkoxide as catalyst may be monoalcohols and polyols such as the beta-hydroxy ester compounds resulting from the ring-opening of the oxirane ring of comprising at least one epoxide group by carboxylic acids, such as the reaction product of the glycidyl ester of neodecanoic acid with carboxylic acids having one to 20 carbon atoms and polycarboxylic acids having two to 54 carbon atoms. As another example, the hydroxyl-functional material may be the reaction product of: (a) a compound comprising at least one epoxide group and (b) a compound selected from hydroxy acids comprising at least one organic acid group and at least one hydroxyl group, polyacids comprising a plurality of organic acid groups and mixtures of these. The compound comprising at least one epoxide group may be a monoepoxide or a polyepoxide. For example, in general a monoepoxide can be prepared by reacting a mono-alcohol or mono-acid with an epihalohydrin or a monounsaturated compound with peroxide or peracetic acid, and a polyepoxide can be prepared by reacting a polyol (including diols, triols, and higher-functionality polyols) with an epihalohydrin or a polyunsaturated compound with peroxide or peracetic acid. Oligomeric or polymeric epoxy-terminated polyglycidyl ethers such as the diglycidyl ether of bisphenol A can also be used. Specifically regarding glycidyl esters, monofunctional glycidyl esters can be prepared by reacting a monofunctional carboxylic acid (e.g., octanoic acid, benzoic acid, benzylic acid, cyclohexane carboxylic acid, and neodecanoic acid) with an epihalohydrin (e.g., epichlorohydrin) under conditions well-known in the art. Polyglycidyl esters may also be used, and can be prepared by reacting a polyfunctional carboxylic acid (e.g., phthalic acid, thioglycolic acid, adipic acid) with an epihalohydrin. Another useful class of monoepoxides are glycidyl ethers. Glycidyl ethers can be prepared by the reaction of monofunctional alcohols (e.g., n-butanol, n-propanol, 2-ethylhexanol, dodecanol, phenol, cresol, cyclohexanol, benzyl alcohol, trimethylolpropane) with an epihalohydrin (e.g., epichlorohydrin). Useful glycidyl ethers include the glycidyl ether of 2-ethanolhexanol, the glycidyl ether of dodecanol, the glycidyl ether of phenol, and the like. Nonlimiting examples of suitable polyglycidyl ethers are the polyglycidyl ethers resulting from the reaction of any of the polyols already mentioned (e.g., 1,6-hexanediol, trimethylolpropane, dimer fatty diols) with an epihalodydrin. Epoxides may also be prepared by reacting a compound containing one or more double bonds with peroxide or peracetic acid under conditions well-known in the art. The epoxide may also be an acrylic-containing polymer or oligomer, preferably deriving its epoxy groups from methacrylate monomer, glycidyl acrylate, allyl glycidyl ether, cyclohexyl monoepoxide methacrylate, the epoxide of the dimer of cylopentadiene methacrylate, or epoxidized butadiene, more preferably glycidyl methacrylate. Epoxide compounds can also be prepared by reacting an isocyanate-terminated component such as a polyisocyanate (including isocyanurates, e.g., the isocyanurate of isophorone diisocyanate) with glycidol. Other known polyepoxides, e.g., epoxy-novolacs, may also be used.

The epoxide group or groups is or are reacted with a compound comprising an organic acid group selected from hydroxy acids having at least one organic acid group and at least one hydroxyl group and, particularly when monoepoxides are used, polyacids comprising a plurality of organic acid groups and which may or may not include hydroxyl groups and any combination of these. The use of a hydroxy acid or polyacid will provide a plurality of hydroxyl groups Useful hydroxy acids include dimethylolpropionic acid, hydroxypivalic acid, malic acid, tartaric acid, and citric acid. Useful polyacids include tricarballylic acid, adipic acid, azeleic acid, trimellitic anhydride, bisphenol F and bisphenol A. The reaction utilizing a hydroxy acid is preferably conducted without catalyst so that unwanted reaction of the hydroxyl groups with the epoxy groups is minimized. The ring-opening of the oxirane ring of an epoxide compound by a carboxylic acid results in a hydroxy ester structure.

In various embodiments, the polyol may be the reaction product of (a) a compound with a molecular weight of up to about 1000 having at least two glycidyl groups and (b) a compound with a molecular weight of up to about 1000, having one hydroxyl or carboxyl group, or having one carboxyl group and one or more hydroxyl groups. From about 0.95 to about 1.05 moles of compound (b) is reacted for each equivalent of glycidyl groups of the compound (a).

The polyglycidyl compound is preferably aliphatic, more preferably cycloaliphatic. The polyglycidyl compound preferably has from 2 to about 4 glycidyl groups, and more preferably 2 glycidyl groups. The polyglycidyl compounds are glycidyl esters, particularly diglycidyl esters. In particular, the polyglycidyl compound may be selected from hexahydrophthalic acid diglycidyl ester, succinic acid diglycidyl ester, and combinations of these. The polyglycidyl compound preferably has a molecular weight of from about 200 to about 500, more preferably from about 300 to about 400. The polyglycidyl compound is reacted with a compound that has an hydroxyl and/or carboxylic acid group. The hydroxyl and/or carboxylic acid group is preferably bound to an aliphatic carbon atom. Particularly preferably, the compound that has the hydroxyl and/or carboxylic acid group is aliphatic. When the compound has a carboxylic acid group, the compound may have from one to about 4 hydroxyl groups. It is possible in that case to avoid polymerization because the acid group reacts at a faster rate than the hydroxyl group or groups. Particular examples of suitable compounds that are reacted with the polyglycidyl compound include, without limitation, monoalcohols such as octanol, 2,2,4-trimethyl-1,3-pentanediol, and cyclohexanol; monocarboxylic acids such as octanoic acid, nonanoic acid, stearic acid, and cyclohexanoic acid; and hydroxycarboxylic acids such as dimethylolpropionic acid; as well as combinations of these compounds. The hydroxyl- and/or carboxyl-functional compound has a molecular weight of up to about 1000, preferably from about 60 to about 500, and more preferably from 100 to about 300.

The reaction may be carried out with a ratio of from about 0.95 to about 1.05 moles the hydroxyl- and/or carboxyl-functional compound for each equivalent of glycidyl groups of the polyglycidyl compound. Thus, on average, only about one carboxyl or hydroxyl group of each compound reacts with a glycidyl group. A catalyst for the reaction may be employed, for example tertiary amines such as triethylamine. Reaction conditions typical for such reactions and esterification reactions may be used. The polyol formed preferably has a molecular weight of from about 200 to about 1000, more preferably from about 300 to about 900, and even more preferably from about 400 to about 800.

In other embodiments, the hydroxyl-functional material that is transcarbamated or transcarbamoylated may be a polymer, such as a polyester polyol, a polyether polyol, a polyhydroxy polycarbonate, a polyurethane polyol, a polyvinyl polyol, particularly an acrylic (polyacrylate) polymer polyol, polyhydroxy polyesteramides, a polysiloxane polyol, or a polyhydroxy polythioether. Acrylic polymers or polyacrylate polymers may be copolymers of both acrylic and methacrylic monomers as well as other copolymerizable vinyl monomers. The term "(meth)acrylate" is used for convenience to designate either or both acrylate, and methacrylate, and the term "(meth)acrylic" is used for convenience to designate either or both acrylic and methacrylic.

Oligomeric and polymeric ethers may be used, including diethylene glycol, triethylene glycol, tetraethylene glycol, pentaethylene glycol, dipropylene glycol, tripropylene glycol, linear and branched polyethylene glycols, polypropylene glycols, and block copolymers of poly(ethylene oxide-co-propylene oxide). Other polymeric polyols may be obtained by reacting a polyol initiator, e.g., a diol such as 1,3-propanediol or ethylene or propylene glycol or a polyol such as trimethylolpropane or pentaerythritol, with a lactone or alkylene oxide chain-extension reagent. Lactones that can be ring opened by an active hydrogen are well-known in the art. Examples of suitable lactones include, without limitation, ε-caprolactone, γ-caprolactone, β-butyrolactone, β-propriolactone, γ-butyrolactone, α-methyl-γ-butyrolactone, β-methyl-γ-butyrolactone, γ-valerolactone, δ-valerolactone, γ-decanolactone, δ-decanolactone, γ-nonanoic lactone, γ-octanoic lactone, and combinations of these. In one preferred embodiment, the lactone is ε-caprolactone. Useful catalysts include those mentioned above for polyester synthesis. Alternatively, the reaction can be initiated by forming a sodium salt of the hydroxyl group on the molecules that will react with the lactone ring. Similar polyester polyols may be obtained by reacting polyol initiator molecules with hydroxy acids, such as 12-hydroxystearic acid.

In other embodiments, a polyol initiator compound may be reacted with an oxirane-containing compound to produce a polyether diol to be used in the polyurethane elastomer polymerization. Alkylene oxide polymer segments include, without limitation, the polymerization products of ethylene oxide, propylene oxide, 1,2-cyclohexene oxide, 1-butene oxide, 2-butene oxide, 1-hexene oxide, tert-butylethylene oxide, phenyl glycidyl ether, 1-decene oxide, isobutylene oxide, cyclopentene oxide, 1-pentene oxide, and combinations of these. The oxirane-containing compound is preferably selected from ethylene oxide, propylene oxide, butylene oxide, tetrahydrofuran, and combinations of these. The alkylene oxide polymerization is typically base-catalyzed. The polymerization may be carried out, for example, by charging the hydroxyl-functional initiator compound and a catalytic amount of caustic, such as potassium hydroxide, sodium methoxide, or potassium tert-butoxide, and adding the alkylene oxide at a sufficient rate to keep the monomer available for reaction. Two or more different alkylene oxide monomers may be randomly copolymerized by coincidental addition or polymerized in blocks by sequential addition. Homopolymers or copolymers of ethylene oxide or propylene oxide are preferred. Tetrahydrofuran may be polymerized by a cationic ring-opening reaction using such counterions as $SbF_6^-$, $AsF_6^-$, $PF_6^-$, $SbCl_6^-$, $BF_4^-$, $CF_3SO_3^-$, $FSO_3^-$, and $ClO_4^-$. Initiation is by formation of a tertiary oxonium ion. The polytetrahydrofuran segment can be prepared as a "living polymer" and terminated by reaction with the hydroxyl group of a diol such as any of those mentioned above. Polytetrahydrofuran is also known as polytetramethylene ether glycol (PTMEG). Any of the polyols mentioned above maybe employed as the polyol initiator and extended in this fashion.

Nonlimiting examples of suitable polycarbonate polyols that might be used include those prepared by the reaction of polyols with dialkyl carbonates (such as diethyl carbonate), diphenyl carbonate, or dioxolanones (such as cyclic carbonates having five- and six-member rings) in the presence of catalysts like alkali metal, tin catalysts, or titanium compounds. Useful polyols include, without limitation, any of those already mentioned. Aromatic polycarbonates are usually prepared from reaction of bisphenols, e.g., bisphenol A, with phosgene or diphenyl carbonate. Aliphatic polycarbonates may be preferred for a higher resistance to yellowing, particularly when the carbamate-functional material is used in an automotive OEM or refinish topcoat.

Polyesters polyols that may be used as the hydroxy-functional material that is transcarbamated may be prepared by reacting: (a) polycarboxylic acids or their esterifiable derivatives, together if desired with monocarboxylic acids, (b) polyols, together if desired with monools, and (c) if desired, other modifying components. Nonlimiting examples of polycarboxylic acids and their esterifiable derivatives include phthalic acid, isophthalic acid, terephthalic acid, halophthalic acids such as tetrachloro- or tetrabromophthalic acid, adipic acid, glutaric acid, azelaic acid, sebacic acid, fumaric acid, maleic acid, trimellitic acid, pyromellitic acid, tetrahydrophthalic acid, hexahydrophthalic acid, 1,2-cyclohexanedicarboxlic acid, 1,3-cyclohexane-discarboxlic acid, 1,4-cyclohexane-dicarboxlic acid, 4-methylhexahydrophthalic acid, endomethylenetetrahydropthalic acid, tricyclodecane-dicarboxlic acid, endoethylenehexahydropthalic acid, camphoric acid, cyclohexanetetracarboxlic acid, and cyclobutanetetracarboxylic acid. The cycloaliphatic polycarboxylic acids may be employed either in their cis or in their trans form or as a mixture of the two forms. Esterifiable derivatives of these polycarboxylic acids include their single or multiple esters with aliphatic alcohols having 1 to 4 carbon atoms or hydroxy alcohols having up to 4 carbon atoms, preferably the methyl and ethyl ester, as well as the anhydrides of these polycarboxylic acids, where they exist. Nonlimiting examples of suitable monocarboxylic acids that can be used together with the polycarboxylic acids include benzoic acid, tert-butylbenzoic acid, lauric acid, isonoanoic acid and fatty acids of naturally occurring oils. Nonlimiting examples of suitable polyols include any of those already mentioned above, such as ethylene glycol, butylene glycol, neopentyl glycol, propanediols, butanediols, hexanediols, diethylene glycol, cyclohexanediol, cyclohexanedimethanol, trimethylpentanediol, ethylbutylpropanediol ditrimethylolpropane, trimethylolethane, trimethylolpropane, glycerol, pentaerythritol, dipentaerythritol, tris-hydroxyethyl isocyanate, polyethylene glycol, polypropylene glycol. Nonlimiting examples of monoalcohols that may be used together with the polyols include butanol, octanol, lauryl alcohol, and ethoxylated and propoxylated phenols. Nonlimiting examples of suitable modifying components include compounds which contain a group which is reactive with respect to the functional groups of the polyester, including polyisocyanates and/or diepoxide compounds, and also if desired, monoisocyanates and/or monoepoxide compounds. The polyester polymerization may be carried out by known standard methods, This reaction is conventionally carried out at temperatures of between 180 and 280° C., in the presence if desired of an appropriate esterification catalyst. Typical catalysts for the esterification polymerization are protonic acids, Lewis acids, titanium alkoxides, and dialkyltin oxides, for example lithium octanoate, dibutyltin oxide, dibutyltin dilaurate, para-toluenesulfonic acid under reflux with small quantities of a suitable solvent as entraining agent such as an aromatic hydrocarbon, for example xylene, or a (cyclo)aliphatic hydrocarbon, for example cyclohexane.

Polyurethanes having hydroxyl functional groups are also well known in the art. Examples of suitable polyurethane polyols include polyester-polyurethanes, polyether-polyurethanes, and polycarbonate-polyurethanes, including, without limitation, polyurethanes polymerized using as polymeric diol reactants polyethers and polyesters including polycaprolactone polyesters or polycarbonate diols. These polymeric diol-based polyurethanes are prepared by reaction of the polymeric diol (polyester diol, polyether diol, polycaprolactone diol, polytetrahydrofuran diol, or polycarbonate diol), one or more polyisocyanates, and, optionally, one or more chain extension compounds. Chain extension compounds, as the term is being used, are compounds having two or more functional groups, preferably two functional groups, reactive with isocyanate groups, such as the diols, amino alcohols, and diamines. Preferably the polymeric diol-based polyurethane is substantially linear (i.e., substantially all of the reactants are difunctional).

Diisocyanates used in making the polyurethane polyols may be aromatic, aliphatic, or cycloaliphatic. Useful diisocyanate compounds include, without limitation, isophorone diisocyanate (IPDI), methylene bis-4-cyclohexyl isocyanate (H$_{12}$MDI), cyclohexyl diisocyanate (CHDI), m-tetramethyl xylene diisocyanate (m-TMXDI), p-tetramethyl xylene diisocyanate (p-TMXDI), 4,4'-methylene diphenyl diisocyanate (MDI, also known as 4,4'-diphenylmethane diisocyanate), 2,4- or 2,6-toluene diisocyanate (TDI), ethylene diisocyanate, 1,2-diisocyanatopropane, 1,3-diisocyanatopropane, 1,6-diisocyanatohexane (hexamethylene diisocyanate or HDI), 1,4-butylene diisocyanate, lysine diisocyanate, meta-xylylenediioscyanate and para-xylylenediisocyanate, 4-chloro-1,3-phenylene diisocyanate, 1,5-tetrahydro-naphthalene diisocyanate, 4,4'-dibenzyl diisocyanate, and xylylene diisocyanate (XDI), and combinations of these. Nonlimiting examples of higher-functionality polyisocyanates that may be used in limited amounts to produce branched thermoplastic polyurethanes (optionally along with monofunctional alcohols or monofunctional isocyanates) include 1,2,4-benzene triisocyanate, 1,3,6-hexamethylene triisocyanate, 1,6,11-undecane triisocyanate, bicycloheptane triisocyanate, triphenylmethane-4,4',4"-triisocyanate, isocyanurates of diisocyanates, biurets of diisocyanates, allophanates of diisocyanates, and the like.

In various embodiments, the polymeric diol preferably has a weight average molecular weight of at least about 500, more preferably at least about 1000, and even more preferably at least about 1800 and a weight average molecular weight of up to about 10,000, but polymeric diols having weight average molecular weights of up to about 5000, especially up to about 4000, may also be preferred. The polymeric diol advantageously has a weight average molecular weight in the range from about 500 to about 10,000, preferably from about 1000 to about 5000, and more preferably from about 1500 to about 4000. The weight average molecular weights may be determined by ASTM D-4274.

The reaction of the polyisocyanate, polymeric diol, and diol or other chain extension agent is typically carried out at an elevated temperature in the presence of a suitable catalyst, for example tertiary amines, zinc salts, and manganese salts. The ratio of polymeric diol, such as polyester diol, to extender can be varied within a relatively wide range depending largely on the desired hardness or flexibility of the final polyurethane elastomer. For example, the equivalent proportion of polyester diol to extender may be within the range of 1:0 to 1:12 and, more preferably, from 1:1 to 1:8. Preferably, the diisocyanate(s) employed are proportioned such that the overall ratio of equivalents of isocyanate to equivalents of active hydrogen containing materials is within the range of 1:1 to 1:1.05, and more preferably, 1:1 to 1:1.02. The polymeric diol segments typically are from about 35% to about 65% by weight of the polyurethane polymer, and preferably from about 35% to about 50% by weight of the polyurethane polymer.

Polyvinyl polyols, such as acrylic (polyacrylate) polyol polymers that may be used as the hydroxy-functional material that is transcarbamated may be prepared by polymerizing one or more hydroxyl-functional, ethylenically unsaturated monomers with one or more other ethylenically unsaturated monomers. Suitable examples of hydroxy-functional ethylenically unsaturated mo Hydroxyl-containing monomers include hydroxy alkyl esters of acrylic or methacrylic acid. Nonlimiting examples of hydroxyl-functional monomers include hydroxyethyl (meth)acrylate, hydroxypropyl (meth)acrylates, hydroxybutyl (meth)acrylates, hydroxyhexyl (meth)acrylates, propylene glycol mono(meth)acrylate, 2,3-dihydroxypropyl (meth)acrylate, pentaerythritol mono(meth)acrylate, polypropylene glycol mono(meth)acrylates, polyethylene glycol mono (meth)acrylates, reaction products of these with epsilon-caprolactone, and other hydroxyalkyl (meth)acrylates having branched or linear alkyl groups of up to about 10 carbons, and mixtures of these, where the term "(meth)acrylate" indicates either or both of the methacrylate and acrylate esters. Generally, at least about 5% by weight hydroxyl-functional monomer is included in the polymer. Example embodiments include up to about 15% by weight hydroxyl-functional monomer in the polymer. The person skilled in the art will appreciate that hydroxyl groups on a vinyl polymer such as an acrylic polymer can be generated by other means, such as, for example, the ring opening of a glycidyl group, for example from copolymerized glycidyl methacrylate, by an organic acid or an amine. Hydroxyl functionality may also be introduced through thio-alcohol compounds, including, without limitation, 3-mercapto-1-propanol, 3-mercapto-2-butanol, 11-mercapto-1-undecanol, 1-mercapto-2-propanol, 2-mercaptoethanol, 6-mercapto-1-hexanol, 2-mercaptobenzyl alcohol, 3-mercapto-1,2-proanediol, 4-mercapto-1-butanol, and combinations of these. Any of these methods may be used to prepare a useful hydroxyl-functional acrylic polymer.

Examples of suitable comonomers that may be used include, without limitation, α,β-ethylenically unsaturated monocarboxylic acids containing 3 to 5 carbon atoms such as acrylic, methacrylic, and crotonic acids and the alkyl and cycloalkyl esters, nitriles, and amides of acrylic acid, methacrylic acid, and crotonic acid; α,β-ethylenically unsaturated dicarboxylic acids containing 4 to 6 carbon atoms and the anhydrides, monoesters, and diesters of those acids; vinyl esters, vinyl ethers, vinyl ketones, and aromatic or heterocyclic aliphatic vinyl compounds. Representative examples of suitable esters of acrylic, methacrylic, and crotonic acids include, without limitation, those esters from reaction with saturated aliphatic alcohols containing 1 to 20 carbon atoms, such as methyl, ethyl, propyl, isopropyl, n-butyl, isobutyl, tert-butyl, hexyl, 2-ethylhexyl, dodecyl, 3,3,5-trimethylhexyl, stearyl, lauryl, cyclohexyl, alkyl-substituted cyclohexyl, alkanol-substituted cyclohexyl, such as 2-tert-butyl and 4-tert-butyl cyclohexyl, 4-cyclohexyl-1-butyl, 2-tert-butyl cyclohexyl, 4-tert-butyl cyclohexyl, 3,3,5,5,-tetramethyl cyclohexyl, tetrahydrofurfuryl, and isobornyl acrylates, methacrylates, and crotonates; unsaturated dialkanoic acids and anhydrides such as fumaric, maleic, itaconic acids and anhydrides and their mono- and diesters with alcohols such as methanol, ethanol, propanol, isopropanol, butanol, isobutanol, and tert-butanol, like maleic anhydride, maleic acid dimethyl ester and maleic acid monohexyl ester; vinyl acetate, vinyl propionate, vinyl ethyl ether, and vinyl ethyl ketone; styrene, α-methyl styrene, vinyl toluene, 2-vinyl pyrrolidone, and p-tert-butylstyrene.

The acrylic polymer may be prepared using conventional techniques, such as by heating the monomers in the presence of a polymerization initiating agent and optionally a chain transfer agent. The polymerization may be carried out in solution, for example.

Typical initiators are organic peroxides such as dialkyl peroxides such as di-t-butyl peroxide, peroxyesters such as t-butyl peroxy 2-ethylhexanoate, and t-butyl peracetate, peroxydicarbonates, diacyl peroxides, hydroperoxides such as t-butyl hydroperoxide, and peroxyketals; azo compounds such as 2,2'azobis(2-methylbutanenitrile) and 1,1'-azobis(cyclohexanecarbonitrile); and combinations of these. Typical chain transfer agents are mercaptans such as octyl mercaptan, n- or tert-dodecyl mercaptan; halogenated compounds, thiosalicylic acid, mercaptoacetic acid, mercaptoethanol and the other thiol alcohols already mentioned, and dimeric alpha-methyl styrene.

The reaction is usually carried out at temperatures from about 20° C. to about 200° C. The reaction may conveniently be done at the temperature at which the solvent or solvent mixture refluxes, although with proper control a temperature below the reflux may be maintained. The initiator should be chosen to match the temperature at which the reaction is carried out, so that the half-life of the initiator at that temperature should preferably be no more than about thirty minutes. Further details of addition polymerization generally and of polymerization of mixtures including (meth)acrylate monomers is readily available in the polymer art. The solvent or solvent mixture is generally heated to the reaction temperature and the monomers and initiator(s) are added at a controlled rate over a period of time, usually between 2 and 6 hours. A chain transfer agent or additional solvent may be fed in also at a controlled rate during this time. The temperature of the mixture is then maintained for a period of time to complete the reaction. Optionally, additional initiator may be added to ensure complete conversion.

A polysiloxane polyol may be made by hydrosilylating a polysiloxane containing silicon hydrides with an alkyenyl polyoxyalkylene alcohol containing two or three terminal primary hydroxyl groups, for example allylic polyoxyalkylene alcohols such as trimethylolpropane monoallyl ether and pentaerythritol monoallyl ether.

Transcarbamation

The transcarbamation is catalyzed with a titanium (IV) alkoxide. In various embodiments, the titanium (IV) alkoxide catalyst is one or more of titanium (IV) alkoxides in which each alkoxide group has one to eight carbon atoms. The titanium (IV) alkoxide catalyst has n alkoxide groups, where n is an integer from one to four, and has 4-n groups selected from halogen groups, acetylacetonate groups, and ethanolaminato groups. Specific, nonlimiting examples of suitable titanium (IV) alkoxide compounds include titanium (IV) isopropoxide, titanium (IV) butoxide, titanium (IV) tert-butoxide, titanium (IV) ethoxide, titanium (IV) ethylhexyloxide, titanium (IV) methoxide, titanium (IV) propoxide, titanium (IV) (triethanolaminato)isopropoxide, chlorotriisopropoxytitanium(IV), diisopropoxytitanium bis(acetylacetonate), titanium (IV) diisopropoxidebis(2,2,6,6-tetramethyl-3,5-heptanedionate), and titanium (IV) (triethanolaminato) isopropoxide.

The titanium (IV) alkoxide may be used in an amount of at least about 0.13 wt. % based on the total weight of the hydroxyl-functional material and the carbamate compound. The amount of the zirconium acetylacetonate will depend, at least in part, upon the hydroxyl material being transcarbamated and the concentrations of hydroxyl groups and the carbamate groups of the carbamate compound in the reaction medium and can be optimized for specific reactants and reaction conditions by straightforward experimentation. For example, in transcarbamation of a C36 diol (based on dimer fatty acid) the titanium (IV) isopropoxide may be used in an amount of from about 0.13 wt. % to about 0.42 wt. %; a typical useful amount for this reaction is about 0.17 wt %. In transcarbamation of a hydroxyl-functional acrylic copolymer the titanium (IV) isopropoxide may be used in an amount of from about 0.44 wt. % to about 1.58 wt. %; a typical useful amount for this reaction is about 0.63 wt %. The weight percentages of titanium (IV) isopropoxide used are based in each case on the total weight of the hydroxyl-functional material and the carbamate compound.

The transcarbamation is preferably carried out in the absence of oxygen, for example under a nitrogen atmosphere. The nitrogen blanket may be removed as the temperature begins to approach reflux as long as the nitrogen is resumed once reflex is lost. The reaction vessel is equipped with suitable stirring, heating and cooling equipment as well as with a reflux condenser which condenses volatile constituents, for example solvent and alcohol by-product from the transcarbamation reaction. A trap or some other device may also be included for removing the alcohol by-product. The transcarbamation reaction may use toluene to aid in removing the by-product and may be carried out at a temperature in the range of from about 125° C.-139° C., preferably at least about 127° C. or at least about 132° C. and up to about 137° C. or up to about 139° C. An optimum temperature for the transcarbamation reaction may be determined by straightforward experimentation, and depends on factors, as should be expected, such as temperature, reactant concentrations, and solubility in the particular solvent system. As may be expected, a certain minimum temperature may need to be reached for the reaction to progress at a desired rate. Mineral acids such as phosphoric acid should be avoided.

The progress of the transcarbamation reaction may be carried out by monitoring hydroxyl number of the hydroxyl-functional material or by monitoring the amount of by-product alcohol (e.g., methanol for methyl carbamate) collected. In contrast to tin catalysts, which promote side reactions, the titanium (IV) alkoxide catalysis is specific to the transcarbamation reaction, and the amount of by-product alcohol (e.g., methanol when methyl carbamate is used) matches the amount expected from titration of hydroxyl number of the transcarbamated material. Similarly, it is possible to perform further thermal steps, for example vacuum stripping to remove organic volatiles from the carbamate-functional product, without the titanium (IV) alkoxide catalyzing unintended side reactions, in contrast to the prevalence of such side reactions when tin catalysts are used to catalyze transcarbamation. The transcarbamation reaction catalyzed with titanium (IV) alkoxide may provide a conversion of at least about 75% of theoretical total replacement of hydroxyl groups with carbamate groups when byproduct alcohol (e.g., methanol) is removed as it forms, depending upon the temperature of the reaction, the time of the reaction, and the concentrations of the hydroxyl groups, carbamate compound, and titanium (IV) alkoxide.

It is possible to react the carbamate compound hydroxyl groups in the presence of titanium (IV) alkoxide during preparation of a resin or during a polymerization reaction, in particular when the preparation step or polymerization does not depend on a reaction of the hydroxyl group. For example, in a last step of preparing a dendritic or hyperbranched resin in which acetal cleavage or a final reaction of a epoxide-functional compound with carboxyl groups is used to generate hydroxyl groups, the carbamate compounds and titanium (IV) alkoxide could be charged to the reactor during such a final step to introduce the carbamate group upon formation of the hydroxyl group. Also in the case of polymerization of an addition copolymer, in which a monomer bearing hydroxyl groups, the carbamate compound and titanium (IV) alkoxide can be introduced into the reactor before or with the hydroxyl monomer. This allows part or all of the transcarbamation to be completed by the time the initial monomer conversion is finished. The carbamate compounds and titanium (IV) alkoxide could also be introduced at a point during the time the monomer mixture is introduced into the reactor or after all of the monomers have been introduced into the reactor.

The polymerization and transcarbamation reactions are carried out in an organic solvent or mixture of organic solvents that is inert toward the monomers used. Examples of suitable solvents include aromatic hydrocarbons, for example toluene, xylene, mesitylene, 2-, 3-, or 4-ethyltoluene, naphthas, as well as higher-boiling aliphatic and cycloaliphatic hydrocarbons, for example various white spirits, mineral turpentine, tetralin and decalin, and also ketones, individually or as mixtures.

Coating Compositions

The product carbamate-functional materials may be formulated into a curable coating composition. Such a composition may be cured by a reaction of the carbamate-functional material or materials with a curing agent that is a compound having a plurality of functional groups that are reactive with the carbamate groups on the polymer. Such reactive groups include active methylol, methylalkoxy or butylalkoxy groups on aminoplast crosslinking agents. Aminoplasts, or amino resins, are described in *Encyclopedia of Polymer Science and Technology* vol. 1, p. 752-789 (1985), the disclosure of which is hereby incorporated by reference. An aminoplast is obtained by reaction of an activated nitrogen with a lower molecular weight aldehyde, optionally with further reaction with an alcohol (preferably a mono-alcohol with one to four carbon atoms such as methanol, isopropanol, n-butanol, isobutanol, etc.) to form an ether group. Preferred examples of activated nitrogens are activated amines such as melamine, benzoguanamine, cyclohexylcarboguanamine, and acetoguanamine; ureas, including urea itself, thiourea, ethyleneurea, dihydroxyethyleneurea, and guanylurea; glycoluril; amides, such as dicyandiamide; and carbamate functional compounds having at least one primary carbamate group or at least two secondary carbamate groups. The activated nitrogen is reacted with a lower molecular weight aldehyde. The aldehyde may be selected from formaldehyde, acetaldehyde, crotonaldehyde, benzaldehyde, or other aldehydes used in making aminoplast resins, although formaldehyde and acetaldehyde, especially formaldehyde, are preferred. The activated nitrogen groups are at least partially alkylolated with the aldehyde, and may be fully alkylolated; preferably the activated nitrogen groups are fully alkylolated. The reaction may be catalyzed by an acid, e.g. as taught in U.S. Pat. No. 3,082,180, the contents of which are incorporated herein by reference.

The optional alkylol groups formed by the reaction of the activated nitrogen with aldehyde may be partially or fully etherified with one or more monofunctional alcohols. Suitable examples of the monofunctional alcohols include, without limitation, methanol, ethanol, n-propanol, isopropanol, n-butanol, isobutanol, tert-butyl alcohol, benzyl alcohol, and so on. Monofunctional alcohols having one to four carbon atoms and mixtures of these are preferred. The etherification may be carried out, for example, by the processes disclosed in U.S. Pat. Nos. 4,105,708 and 4,293,692, the disclosures of which are incorporated herein by reference. The aminoplast may be at least partially etherified, and in various embodiments the aminoplast is fully etherified. For example, the aminoplast compounds may have a plurality of methylol and/or etherified methylol, butylol, or alkylol groups, which may be present in any combination and along with unsubstituted nitrogen hydrogens. Examples of suitable curing agent compounds include, without limitation, melamine formaldehyde resins, including monomeric or polymeric melamine resins and partially or fully alkylated melamine resins, and urea resins (e.g., methylol ureas such as urea formaldehyde resin, and alkoxy ureas such as butylated urea formaldehyde resin). One nonlimiting example of a fully etherified melamine-formaldehyde resin is hexamethoxymethyl melamine.

The alkylol groups are capable of self reaction to form oligomeric and polymeric materials. Useful materials are characterized by a degree of polymerization. For melamine formaldehyde resins, it is preferred to use resins having a number average molecular weight less than about 2000, more preferably less than 1500, and even more preferably less than 1000.

A coating composition including the product carbamate-functional materials and aminoplast crosslinking agents may further include a strong acid catalyst to enhance the cure reaction. Such catalysts are well-known in the art and include, for example, para-toluenesulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine.

The amount of the product carbamate-functional materials and the aminoplast crosslinker in the coating composition may be varied widely and is typically 8 wt % to 20 wt % by weight, preferably 10 wt % to 16 wt % by weight, of the product carbamate-functional material or materials based on the total weight of product carbamate-functional materials and aminoplast crosslinker.

A solvent may optionally be utilized in the coating compositions. Although the coating composition may be formulated, for example, in the form of a powder, it is often desirable that the composition be in a substantially liquid state, which can be accomplished with the use of a solvent to either dissolve or disperse the product carbamate-functional material or materials and aminoplast crosslinker. In general, depending on the solubility characteristics of the components, the solvent can be any organic solvent and/or water. In one preferred embodiment, the solvent is a polar organic solvent. More preferably, the solvent is a polar aliphatic solvent or polar aromatic solvent. Still more preferably, the solvent is a ketone, ester, acetate, aprotic amide, aprotic sulfoxide, or aprotic amine. Examples of useful solvents include methyl ethyl ketone, methyl isobutyl ketone, n-amyl acetate, ethylene glycol butyl ether acetate, propylene glycol monomethyl ether acetate, xylene, N-methylpyrrolidone, or blends of aromatic hydrocarbons. In another preferred embodiment, the product carbamate-functional materials and aminoplast crosslinker are dispersed in water or a mixture of water with small amounts of organic water-soluble or -miscible co-solvents. The solvent present in the coating composition is preferably in an amount of from about 0.01 weight percent to about 99 weight percent, preferably from about 10 weight percent to about 60 weight percent, and more preferably from about 30 weight percent to about 50 weight percent. The solvent or solvent mixture may be composed of aromatic hydrocarbons such as 1,2,4-trimethylbenzene, mesitylene, xylene, propylbenzene and isopropylbenzene. One example of a suitable solvent mixture comprising aromatic hydrocarbons is solvent naphtha. The solvent may also be composed of aliphatic hydrocarbons, ketones such as acetone, methyl ethyl ketone or methyl amyl ketone, esters such as ethyl acetate, butyl acetate, pentyl acetate or ethyl ethoxy propionate, ethers or mixtures of the aforementioned solvents. Examples of such solvents are aliphatic and/or aromatic hydrocarbons such as toluene, xylene, solvent naphtha, and mineral spirits, ketones, such as acetone, methyl ethyl ketone or methyl amyl ketone, esters, such as ethyl acetate, butyl acetate, pentyl acetate or ethyl ethoxypropionate, ethers such as glycol ethers like propylene glycol monomethyl ether, alcohols such as ethanol, propanol, isopropanol, n-butanol, isobutanol, and tert-butanol, nitrogen-containing compounds such as N-methyl pyrrolidone and N-ethyl pyrrolidone, and combinations of these.

When the coating compositions are formulated as basecoat topcoats, monocoat topcoats, or primers they contain pigments and fillers, including special effect pigments. Nonlimiting examples of special effect pigments that may be utilized in basecoat and monocoat topcoat coating compositions include metallic, pearlescent, and color-variable effect flake pigments. Metallic (including pearlescent, and color-variable) topcoat colors are produced using one or more special flake pigments. Metallic colors are generally defined as colors having gonioapparent effects. For example, the American Society of Testing Methods (ASTM) document F284 defines metallic as "pertaining to the appearance of a gonioapparent material containing metal flake." Metallic basecoat colors may be produced using metallic flake pigments like aluminum flake pigments, coated aluminum flake pigments, copper flake pigments, zinc flake pigments, stainless steel flake pigments, and bronze flake pigments and/or using pearlescent flake pigments including treated micas like titanium dioxide-coated mica pigments and iron oxide-coated mica pigments to give the coatings a different appearance (degree of reflectance or color) when viewed at different angles. Metal flakes may be cornflake type, lenticular, or circulation-resistant; micas may be natural, synthetic, or aluminum-oxide type. Flake pigments do not agglomerate and are not ground under high shear because high shear would break or bend the flakes or their crystalline morphology, diminishing or destroying the gonioapparent effects. The flake pigments are satisfactorily dispersed in a binder component by stirring under low shear. The flake pigment or pigments may be included in the high solids coating composition in an amount of about 0.01 wt. % to about 0.3 wt. % or about 0.1 wt. % to about 0.2 wt. %, in each case based on total binder weight. Nonlimiting examples of commercial flake pigments include PALIOCROME® pigments, available from BASF Corporation.

Nonlimiting examples of other suitable pigments and fillers that may be utilized in basecoat and monocoat topcoat coating compositions include inorganic pigments such as titanium dioxide, barium sulfate, carbon black, ocher, sienna, umber, hematite, limonite, red iron oxide, transparent red iron oxide, black iron oxide, brown iron oxide, chromium oxide green, strontium chromate, zinc phosphate, silicas such as fumed silica, calcium carbonate, talc, barytes, ferric ammonium ferrocyanide (Prussian blue), and ultramarine, and organic pigments such as metallized and non-metallized azo reds, quinacridone reds and violets, perylene reds, copper phthalocyanine blues and greens, carbazole violet, monoarylide and diarylide yellows, benzimidazolone yellows, tolyl orange, naphthol orange, nanoparticles based on silicon dioxide, aluminum oxide or zirconium oxide, and so on. The pigment or pigments are preferably dispersed in a resin or polymer or with a pigment dispersant, such as binder resins of the kind already described, according to known methods. In general, the pigment and dispersing resin, polymer, or dispersant are brought into contact under a shear high enough to break the pigment agglomerates down to the primary pigment particles and to wet the surface of the pigment particles with the dispersing resin, polymer, or dispersant. The breaking of the agglomerates and wetting of the primary pigment particles are important for pigment stability and color development. Pigments and fillers may be utilized in amounts typically of up to about 60% by weight, based on total weight of the coating composition. The amount of pigment used depends on the nature of the pigment and on the depth of the color and/or the intensity of the effect it is intended to produce, and also by the dispersibility of the pigments in the pigmented coating composition. The pigment content, based in each case on the total weight of the pigmented coating composition, is preferably 0.5% to 50%, more preferably 1% to 30%, very preferably 2% to 20%, and more particularly 2.5% to 10% by weight.

Clearcoat coating compositions typically include no pigment, but may include small amount of colorants or fillers that do not unduly affect the transparency or desired clarity of the clearcoat coating layer produced from the composition.

Additional desired, customary coating additives agents may be included, for example, surfactants, stabilizers, wetting agents, dispersing agents, adhesion promoters, UV absorbers, hindered amine light stabilizers such as HALS compounds, benzotriazoles or oxalanilides; free-radical scavengers; slip additives; defoamers; reactive diluents, of the kind which are common knowledge from the prior art; wetting agents such as siloxanes, fluorine compounds, carboxylic monoesters, phosphoric esters, polyacrylic acids and their copolymers, for example polybutyl acrylate, or polyurethanes; adhesion promoters such as tricyclodecanedimethanol; flow control agents; film-forming assistants such as cellulose derivatives; rheology control additives, such as the additives known from patents WO 94/22968, EP-A-0 276 501, EP-A-0 249 201 or WO 97/12945; crosslinked polymeric microparticles, as disclosed for example in EP-A-0 008 127; inorganic phyllosilicates such as aluminum-magnesium silicates, sodium-magnesium and sodium-magnesium-fluorine-lithium phyllosilicates of the montmorillonite type; silicas such as Aerosils®; or synthetic polymers containing ionic and/or associative groups such as polyvinyl alcohol, poly (meth)acrylamide, poly(meth)acrylic acid, polyvinylpyrrolidone, styrene-maleic anhydride copolymers or ethylene-maleic anhydride copolymers and their derivatives, or hydrophobically modified ethoxylated urethanes or polyacrylates; flame retardant; and so on. Typical coating composition include one or a combination of such additives.

Coating compositions can be coated by any of a number of techniques well-known in the art. These include, for example, spray coating, dip coating, roll coating, curtain coating, and the like. For automotive body panels, spray coating is preferred. The coating compositions of the invention can be applied by any of the typical application methods, such as spraying, knife coating, spreading, pouring, dipping, impregnating, trickling or rolling, for example. In the course of such application, the substrate to be coated may itself be at rest, with the application equipment or unit being moved. Alternatively the substrate to be coated, in particular a coil, may be moved, with the application unit at rest relative to the substrate or being moved appropriately. Preference is given to employing spray application methods, such as compressed-air spraying, airless spraying, high-speed rotation, electrostatic spray application, alone or in conjunction with hot spray application such as hot-air spraying, for example.

The coating compositions and coating systems of the invention, especially the clearcoat systems, are employed in particular in the technologically and esthetically particularly demanding field of automotive OEM finishing and also of automotive refinish. With particular preference the coating compositions of the invention are used in multistage coating methods, particularly in methods where a pigmented basecoat film is first applied to an uncoated or precoated substrate and thereafter a film with the coating compositions of the invention is applied. The invention, accordingly, also provides multicoat effect and/or color coating systems comprising at least one pigmented basecoat and at least one clearcoat disposed thereon, wherein the clearcoat has been produced from the coating composition containing the product carbamate-functional materials as disclosed herein.

When the coating composition is used as the clearcoat of a composite color-plus-clear coating, the pigmented basecoat composition may be a coating composition containing the disclosed product carbamate-functional materials or may be any of a number of types well-known in the art, and does not require explanation in detail herein. Polymers known in the art to be useful in basecoat compositions include acrylics, vinyls, polyurethanes, polycarbonates, polyesters, alkyds, and polysiloxanes. Preferred polymers include acrylics and polyurethanes. In one preferred embodiment of the invention, the basecoat composition also utilizes a carbamate-functional acrylic polymer. Basecoat polymers may be thermoplastic, but are preferably crosslinkable and comprise one or more type of crosslinkable functional groups. Such groups include, for example, hydroxy, isocyanate, amine, epoxy, acrylate, vinyl, silane, and acetoacetate groups. These groups may be masked or blocked in such a way so that they are unblocked and available for the crosslinking reaction under the desired curing conditions, generally elevated temperatures. Basecoat polymers may be self-crosslinkable or may require a separate crosslinking agent that is reactive with the functional groups of the polymer. When the polymer comprises hydroxy functional groups, for example, the crosslinking agent may be an aminoplast resin, isocyanate and blocked isocyanates (including isocyanurates), and acid or anhydride functional crosslinking agents.

Not only water-thinnable basecoat materials but also basecoat materials based on organic solvents can be used. Suitable basecoat materials are described for example in EP-A-0 692 007 and in the documents cited there in column 3 lines 50 et seq. The applied basecoat material is preferably first dried, i.e., at least some of the organic solvent and/or water is stripped from the basecoat film in an evaporation phase. Drying is accomplished preferably at temperatures from room temperature to 80° C. Drying is followed by the application of the coating composition of the invention. Subsequently the two-coat system is baked, preferably under conditions employed for automotive OEM finishing, at temperatures from 30 to 200° C., more preferably 40 to 190° C., and in particular 50 to 180° C., for a time of 1 min up to 10 h, more preferably 2 min up to 5 h, and in particular 3 min to 3 h, although longer cure times may also be employed at the temperatures employed for automotive refinish, which are preferably between 30 and 90° C.

The coating compositions are preferably subjected to conditions so as to cure the coating layers. The applied coating compositions can be cured after a certain rest time or "flash" period. The rest time serves, for example, for the leveling and devolatilization of the coating films or for the evaporation of volatile constituents such as solvents. The rest time may be assisted or shortened by the application of elevated temperatures or by a reduced humidity, provided this does not entail any damage or alteration to the coating films, such as premature complete crosslinking, for instance. The thermal curing of the coating compositions has no peculiarities in terms of method but instead takes place in accordance with the typical, known methods such as heating in a forced-air oven or irradiation with IR lamps. The thermal cure may also take place in stages. Another preferred curing method is that of curing with near infrared (NIR) radiation. Although various methods of curing may be used, heat-curing is preferred. Generally, heat curing is effected by exposing the coated article to elevated temperatures provided primarily by radiative heat sources. The thermal cure takes place advantageously at a temperature of 30 to 200° C., more preferably 40 to 190° C., and in particular 50 to 180° C. for a time of 1 min up to 10 h, more preferably 2 min up to 5 h, and in particular 3 min to 3 h, although longer cure times may be employed in the case of the temperatures that are employed for automotive refinish, which are preferably between 30 and 90° C. Curing temperatures will vary depending on the particular crosslinking agents, however they generally range between 93° C. and 177° C., preferably between 115° C. and 150° C., and more preferably at temperatures between 115° and 138° C. for a blocked acid catalyzed system. For an unblocked acid catalyzed system, the cure temperature is preferably between 82° C. and 125° C. The curing time will vary depending on the particular components used, and physical parameters such as the thickness of the layers, however, typical curing times range from about 15 to about 60 minutes, and preferably about 15-25 minutes for blocked acid catalyzed systems and about 10-20 minutes for unblocked acid catalyzed systems.

The cured basecoat layers formed may have a thickness of from about 5 to about 75 µm, depending mainly upon the color desired and the thickness needed to form a continuous layer that will provide the color. The cured clearcoat layers formed typically have thicknesses of from about 30 µm to about 65 µm.

The coating composition can be applied onto many different types of substrates, including metal substrates such as bare steel, phosphated steel, galvanized steel, or aluminum; and non-metallic substrates, such as plastics and composites. The substrate may also be any of these materials having upon it already a layer of another coating, such as a layer of an electrodeposited primer, primer surfacer, and/or basecoat, cured or uncured.

The substrate may be first primed with an electrodeposition (electrocoat) primer. The electrodeposition composition can be any electrodeposition composition used in automotive vehicle coating operations. Non-limiting examples of electrocoat compositions include the CATHOGUARD® electrocoating compositions sold by BASF Corporation. Electrodeposition coating baths usually comprise an aqueous dispersion or emulsion including a principal film-forming epoxy resin having ionic stabilization (e.g., salted amine groups) in water or a mixture of water and organic cosolvent. Emulsified with the principal film-forming resin is a crosslinking agent that can react with functional groups on the principal resin under appropriate conditions, such as with the application of heat, and so cure the coating. Suitable examples of crosslinking agents, include, without limitation, blocked polyisocyanates. The electrodeposition coating compositions usually include one or more pigments, catalysts, plasticizers, coalescing aids, antifoaming aids, flow control agents, wetting agents, surfactants, UV absorbers, HALS compounds, antioxidants, and other additives.

The electrodeposition coating composition is preferably applied to a dry film thickness of 10 to 35 µm. After application, the coated vehicle body is removed from the bath and rinsed with deionized water. The coating may be cured under appropriate conditions, for example by baking at from about 135° C. to about 190° C. for between about 15 and about 60 minutes.

Because the coatings of the invention produced from the coating compositions of the invention adhere excellently even to electrocoats, surfacer coats, basecoat systems or typical, known clearcoat systems that have already cured, they are outstandingly suitable not only for use in automotive OEM finishing but also for automotive refinish or for the modular scratchproofing of automobile bodies that have already been painted.

The following examples illustrate, but do not in any way limit, the scope of the methods and compositions as described and claimed. All parts are parts by weight unless otherwise noted.

Examples

Example 1 of the Invention

Transcarbamation of Diol

A dicarbamate was prepared from a diol using titanium (IV) isopropoxide as catalyst as follows. A reactor equipped with a stirrer, heating mantle, and reflux column including a partial condenser and a reflux condenser connected to a Dean-Stark trap. The reactor was charged with 450 g Pripol™ 2030 (1.68 eq, Dimer diol, obtained from Croda Coatings & Polymers) followed by 152.8 g methyl carbamate (2.03 eq), 1.031 g titanium (IV) isopropoxide (0.0035 mole), and 175.37 g toluene. An equivalent excess of methyl carbamate was used to ensure the complete conversion of hydroxyl groups to carbamate groups. The contents of the reactor were heated to reflux with continuous stirring. The contents of the reactor were kept under a nitrogen purge until reflux began, after which the flow of nitrogen was halted. Azeotrope was collected in the trap over a total period of eight hours, while the temperature of the reaction mixture increased from about 132° C. to about 138° C. A total of about 74 grams of azeotrope was collected, which contained approximately 51 grams of methanol. The percent conversion was calculated to be 97.52% based on measurement of residual hydroxyl groups. The product dicarbamate had a nonvolatile content of 77.52% by weight and a measured hydroxyl number of 4.49 g KOH/g nonvolatile. The product dicarbamate is colorless (color=1 on the Gardner scale, measured according to ASTM D1544) with a haze.

Example 2 of the Invention

Transcarbamation of Acrylic polymer Using a Modified Procedure

A reactor equipped with a stirrer, heating mantle, monomer add line, and distillation column including a partial condenser and a reflux condenser connected to a Dean-Stark trap. The reactor was charged with 352.4 grams methyl carbamate, 552 grams and Solvesso 100. The contents of the flask were heating with stirring to 140° C. A monomer mixture of 587.6 grams hydroxyethyl methacrylate, 5.8 grams methacrylic acid, 823.3 grams ethylhexyl acrylate, 115.6 grams ethylhexyl methacrylate, 115.6 grams sytrene, 198.6 grams Vazo® 67 (2,2'azobis-(2-methylbutyronitrile, obtained from DuPont), and 227 grams toluene was added at a uniform rate over a period of 4.5 hours. Upon completion of the acrylic monomer feed the reaction mixture was held at 140° C. for one hour. The reaction mixture was cooled down to room temperature after which 13.24 grams of titanium (IV) isopropoxide, tri-isodecyl phosphite 2.22 gms and 709.2 grams of toluene were added to the reactor. The contents were stirred and heated to a reflux temperature observed to be 125.2° C. The reflux temperature reached a final temperature of 130.9° C. over a total of 44 hours as the reaction proceeded, then the reaction mixture was cooled. A total of grams of azeotrope 150 gms was collected. The measured hydroxyl number based on residual hydroxyl groups was 32.91 mg KOH/gms and the total percent conversion of hydroxy groups was thus calculated to be 75.43%. The carbamated acrylic polymer was a clear, dark yellow. The polymer was further vacuum stripped and thinned down in Solvesso 100 solvent to yield a nonvolatile content of 72.41% by weight nonvolatiles. The product had a color of 5 on the Gardner scale, measured according to ASTM D1544.

Comparative Examples A-G

The procedure of Example 1 was followed using the amounts of materials shown in Table 1 for each of Comparative Examples A-G. Amounts are reported in grams. The % conversion was measured after the time indicated in the table.

| Comparative Example | C36 Diol* | Methyl carbamate | Catalyst, amount | Toluene | % Conversion (hours at reflux) | Minimum Reflux Temp. (° C.) |
|---|---|---|---|---|---|---|
| A | 450 | 152.8 | Aluminum Chelate[1], 2.32 | 175.37 | 0% (4.3) | 132.2 |
| B | 450 | 147.45 | bismuth oxide, 1.67 | 175.37 | 0% (3.25) | 133.5 |
| C | 450 | 147.45 | zinc acetylacetonate, 0.94 | 175.37 | 0% (4) | 132.4 |
| D | 450 | 147.45 | zinc oxalate, 0.545 | 175.37 | 0% (3.5) | 132.9 |
| E | 450 | 147.45 | zinc acetate, 0.78 | 175.37 | 0% (2) | 132.1 |
| F | 450 | 147.45 | bismuth carboxylate, 2.27 | 175.37 | 0% (4.75) | 132.2 |
| G | 450 | 147.5 | Zirconium chelate[2], 7.77 | 175.4 | 0% (5) | 132.3 |

*Pripol ™ 2030 or Pripol ™ 2033
[1]CGX PEB 109. obtained from BASF
[2]K-KAT ® XC 6212, obtained from King Industries. Norwalk, CT The minimum reflux temperature for transcarbamation is believed to reflect solubility of the catalyst in the toluene-containing reaction medium. This temperature was lower for the syntheses performed using the titanium(IV) isopropoxide catalyst than for any of the comparative examples.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of preparing a carbamate-functional material, comprising reacting a carbamate compound having the structure

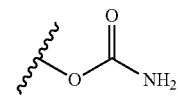

with a hydroxy-functional material using a titanium (IV) alkoxide catalyst.

2. The method according to claim 1, wherein the titanium (IV) alkoxide catalyst has n alkoxide groups, wherein n is an integer from one to four, and 4-n groups selected from halogen groups, acetylacetonate groups, and ethanolaminato groups.

3. The method according to claim 1, wherein each alkoxide group has one to eight carbon atoms.

4. The method according to claim 1, wherein the titanium (IV) alkoxide catalyst comprises titanium (IV) isopropoxide.

5. The method according to claim 1, wherein the carbamate compound is an alkyl carbamate.

6. The method according to claim 1, wherein the carbamate compound is selected from the group consisting of methyl carbamate, ethyl carbamate, n-propyl carbamate, isopropyl carbamate, n-butyl carbamate, isobutyl carbamate, tert-butyl carbamate, n-hexyl carbamate, 2-ethylhexyl carbamate, cyclohexyl carbamate, phenyl carbamate, and combinations thereof.

7. The method according to claim 1, wherein the hydroxy-functional material is a monomeric compound having from 1 to 160 carbon atoms.

8. The method according to claim 1, wherein the hydroxy-functional material has from 12 to 72 carbon atoms and at least two hydroxyl groups.

9. The method according to claim 1, wherein the hydroxy-functional material comprises dimerized, trimerized, tetramerized or high oligomer addition products of unsaturated fatty acids having 12 to 18 carbon atoms and having carboxylic acid groups which have been reduced.

10. The method according to claim 1, wherein the hydroxy-functional material is a hyperbranched polyol.

11. The method according to claim 10, wherein reaction is carried out during a final step of making the hyperbranched polyol.

12. The method according to claim 1, wherein the hydroxy-functional material is a member selected from the group consisting of polyester polyols, polyether polyols, polyhydroxy polycarbonates, polyurethane polyols, polyvinyl polymer polyols, polyhydroxy polyesteramides, polysiloxane polyols, and polyhydroxy polythioethers.

13. The method according to claim 12, wherein the reaction is carried out during polymerization of the hydroxy-functional material.

14. The method according to claim 1, wherein the titanium (IV) alkoxide is used in an amount of from about 0.13 wt. % to about 1.6 wt. % based on the total weight of the hydroxyl-functional material and the carbamate compound.

15. The method according to claim 1, wherein the reaction is carried out at a temperature in the range of from about 125° C. to about 139° C.

16. The method according to claim 1, wherein the reaction product has at least about 75% of theoretical total replacement of hydroxyl groups with carbamate groups.

17. A method of preparing a carbamate-functional material, comprising reacting a carbamate compound with a hyperbranched polyol using a titanium (IV) alkoxide catalyst.

* * * * *